(12) United States Patent
Osawa et al.

(10) Patent No.: US 6,187,926 B1
(45) Date of Patent: Feb. 13, 2001

(54) PROCESS FOR PRODUCING QUINOLONE DERIVATIVES

(75) Inventors: Tatsushi Osawa; Kazuo Kubo; Hideko Murooka; Tatsuo Nakajima, all of Takasaki (JP)

(73) Assignee: Kirin Beer Kabushiki Kaisha, Tokyo-to (JP)

( * ) Notice: Under 35 U.S.C. 154(b), the term of this patent shall be extended for 0 days.

(21) Appl. No.: 09/420,521

(22) Filed: Oct. 18, 1999

Related U.S. Application Data

(63) Continuation of application No. PCT/JP98/01708, filed on Apr. 15, 1998.

(30) Foreign Application Priority Data

Apr. 18, 1997 (JP) .................................................. 9 -101220

(51) Int. Cl.$^7$ ..................... C07D 215/233; C07D 215/40
(52) U.S. Cl. ........................... 546/156; 546/153; 546/262
(58) Field of Search ..................................... 546/262, 153, 546/156

(56) References Cited

U.S. PATENT DOCUMENTS 5,225,418 * 7/1993 Miller .................... 514/285
5,571,822 * 11/1996 Lee et al. .............................. 514/312

FOREIGN PATENT DOCUMENTS

| 0 343 574 | 11/1989 | (EP) . |
| 56-92289 | 7/1981 | (JP) . |
| 1-224363 | 9/1989 | (JP) . |

OTHER PUBLICATIONS

Justus K. Landquist, "Synthetic Antimalarials. Part XLVI. Some 4–Dialkyl–Aminoalkylaminoquinoline Derivatives", Journal of the Chemical Society, pp. 1038–1044, 1951.

* cited by examiner

*Primary Examiner*—Alan L. Rotman
*Assistant Examiner*—Rita Desai
(74) *Attorney, Agent, or Firm*—Oblon, Spivak, McClelland, Maier & Neustadt, P.C.

(57) ABSTRACT

The present invention relates to a process for producing a 4-quinolone derivative, comprising allowing an o-aminoacetophenone derivative to react with a formic acid in an aprotic solvent in the presence of a suitable base, and adding a protic solvent to the reaction mixture. This is a simple process for producing 4-quinolone derivatives, applicable to large-scale commercial production.

21 Claims, No Drawings

PROCESS FOR PRODUCING QUINOLONE DERIVATIVES

This application is a Continuation of International Application PCT/JP98/01708, filed on Apr. 15, 1998.

TECHNICAL FIELD

The present invention relates to a novel process for producing quinolone derivatives, and, more particularly, to a novel process for producing 2,3-unsubstituted 4-quinolone derivatives. The derivatives produced by the process of the present invention can be used as important intermediates in the production of final products to be used as pharmaceuticals, agricultural chemicals, or the like.

BACKGROUND ART

The following are common processes for producing 2,3-unsubstituted 4-quinolone derivatives. For example, there have been known, as processes for producing 7-chloroquinolone or 5,6,7,8-polysubstituted quinolones, a process comprising allowing an aniline derivative to react with an alkoxymethylene malonic ester in a solvent under high temperature conditions (*Organic Synthesis*, Vol. 3, pp. 272–275 (1955); *Acta Chim. Hung.*, Vol. 112, pp. 241–247 (1983)), a process comprising allowing an aniline derivative to react with a propiolic ester in a solvent under high temperature conditions (*Tetrahedron*, Vol. 41, pp. 3033–3036 (1985)), and a process that is conducted in a gaseous phase under high temperature conditions (*J. Chem. Soc. Chem. Commun.*, pp. 957–958 (1983)). These conventional processes are summarized in the following Table.

producing 2,3-unsubstituted 4-quinolone derivatives. It is the present situation that there is a demand for a simpler process free from the foregoing problems.

An object of the present invention is therefore to provide a novel process for producing 2,3-unsubstituted quinolone derivatives by overcoming the aforementioned problems encountered in the conventional processes.

DISCLOSURE OF THE INVENTION

We earnestly made studies in order to attain the above object. As a result, it was found that a 2,3-unsubstituted 4-quinolone derivative can be produced under mild conditions by allowing an o-aminoacetophenone derivative to react with a formic ester in an aprotic solvent in the presence of a suitable base, and adding a protic solvent to the reaction mixture. The present invention was accomplished on the basis of this finding.

The present invention provides a process for producing a quinolone derivative represented by general formula (I):

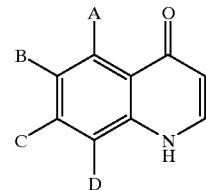

(I)

in which A to D are independently selected from the group

TABLE

Conventional Processes for Producing 2,3-Unsubstituted 4-Quinolone Derivatives

| | Literature | Starting Compound | Number of Steps | Conditions | Reaction Product | Yield |
|---|---|---|---|---|---|---|
| 1 | Organic Synthesis Vol. 3 pp. 272–275 (1955) | m-chloroaniline | 4 | heating to 250° C. in 2 steps | 7-chloro-4-quinolone | unknown |
| 2 | Acta Chim. Hung Vol. 112, pp. 241–247 (1983) | 3,4-methylenedioxy-aniline | 4 | heating to 120° C. in one step heating in diphyl* under reflux in one step | 6,7-methylene-dioxy-4-quinolone | Sum total 18% |
| 3 | Tetrahedoron Vol. 41, pp. 3033–3036 (1985) | 2,3-dimethoxy-aniline | 1 | heating in diphenyl ether (b.p. 259° C.) under reflux | 7,8-dimethoxy-4-quinolone | 72% |
| 4 | J. Chem. Soc. Chem. Commun. pp. 957–958 (1983) | sec-amine derivative | 1 | in a gaseous phase at 600° C. | 4-quinolone | 90% |

*"diphyl" is a solvent mixture of biphenyl (b.p. 255° C.) and diphenyl ether (b.p. 259° C.), and the boiling point of "diphyl" is also assumed to be approximately 250° C.
Characteristic features of the above conventional processes:
1) All of the processes of Litertures 1 to 4 require heating to high temperature.
2) The processes of Literatures 1 and 2 require multiple steps.
3) The reaction product of Literature 2 is identical with that of Example 3 of the instant invention; and the reaction product of Literature 4 is the same as that of Example 2 of the present invention.

The above-described conventional processes have such disadvantages that they require many steps to be carried out at high temperatures or require high temperature reactions using diphenyl ether as solvent under reflux. They are therefore unsuitable as processes for commercially mass-consisting of hydrogen, lower alkyl, lower alkoxyl, lower alkylcarbonyl, lower alkoxycarbonyl, lower alkylthio, lower alkylamino, di-lower alkylamino, halogen, trifluoromethyl and nitro, comprising allowing an o-amino-acetophenone derivative represented by general formula (II):

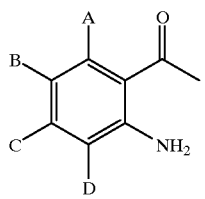

(II)

in which A to D are as defined above, to react with a formic ester in an aprotic solvent in the presence of a base, and adding a protic solvent to the reaction mixture.

BEST MODE FOR CARRYING OUT THE INVENTION

The present invention provides, as mentioned hereinbefore, a process for producing a quinolone derivative represented by the above general formula (I), comprising allowing a compound represented by the above general formula (II) to react with a formic ester in an aprotic solvent in the presence of a base, and adding a protic solvent to the reaction mixture.

All of the lower alkyl, lower alkoxyl, lower alkylcarbonyl, lower alkoxycarbonyl, lower alkylthio, lower alkylamino, and di-lower alkylamino in the definition of A to D in the above general formulas (I) and (II) have a linear or branched lower alkyl moiety of 1 to 6 carbon atoms, such as methyl, ethyl, propyl, isopropyl, butyl, isobutyl, sec-butyl, tert-butyl, pentyl or hexyl. The halogen in the definition denotes fluorine, chlorine, bromine or iodine.

The formic ester that is used in the present invention can include methyl formate, ethyl formate, propyl formate, isopropyl formate, butyl formate, isobutyl formate, sec-butyl formate, tert-butyl formate, and phenyl formate. Methyl or ethyl formate is preferred. These formic esters may be either commercially available or can be obtained by conventional methods.

The formic ester is used in an amount of 3 to 100 equivalents, preferably 5 to 10 equivalents relative to the derivative represented by general formula (II). The formic ester can often be used also in a large amount in excess of the above range. However, it is wasteful, from an economical point of view, to use the formic ester in such a large amount.

The base that is used in the present invention can include carbonates (e.g., potassium carbonate, sodium carbonate, cesium carbonate, etc.), metallic hydrides (e.g., lithium hydride, sodium hydride, potassium hydride, etc., sodium hydride being preferred), and metallic alkoxides (e.g., lithium methoxide, lithium ethoxide, lithium isopropoxide, sodium methoxide, sodium ethoxide, sodium propoxide, sodium isopropoxide, sodium butoxide, sodium isobutoxide, sodium sec-butoxide, sodium tert-butoxide, potassium methoxide, potassium ethoxide, potassium propoxide, potassium isopropoxide, potassium butoxide, potassium isobutoxide, potassium sec-butoxide, potassium tert-butoxide, etc., sodium methoxide and sodium ethoxide being preferred).

The base is used in an amount of 1 to 20 equivalents, preferably 2 to 6 equivalents relative to the derivative represented by general formula (II). The base can often be used also in a large amount exceeding the above-described range. However, the reaction rate is not improved substantially even if such a large amount of the base is used, so that this is wasteful from an economical point of view.

The aprotic solvent for use in the present invention can include aromatic hydrocarbons (e.g., benzene, toluene, chlorobenzene, etc.), ether solvents (e.g., dimethoxyethane, tetrahydrofuran, dioxane, etc.), acetonitrile, and dimethylformamide. Dimethoxyethane, tetrahydrofuran and dioxane are preferred. A solvent mixture of any of these solvents may also be used.

The reaction temperature may vary depending upon the solvent and base used; however, it is generally in the range of −70 to 150° C., preferably in the range of 0 to 100° C. The reaction time may also vary depending upon the other reaction conditions; and it is generally from 10 minutes to 20 hours.

At the end of the above-described period of reaction time, a protic solvent is added to the reaction mixture in an amount of 0.01 to 2 times, preferably 0.02 to 1 time the volume of the aprotic solvent used, thereby terminating the reaction. Examples of the protic solvent include water, methanol, ethanol, propanol, 2-propanol and acetic acid. Water is preferred. The reaction product may be crystallized by adding an aqueous acidic solution (e.g., hydrochloric acid) to the above mixture, and recovered by filtration. Alternatively, the reaction product may be recovered by extraction with an organic solvent such as chloroform. The reaction product obtained is isolated and purified by using, as needed, a conventional method such as column chromatography, distillation or recrystallization.

The reaction products that can be obtained by the process of the present invention are 4-quinolone derivatives, 4-quinolinol derivatives that are tautomers of 4-quinolone derivatives, or mixtures thereof. Further, the reaction products obtained by the process of the present invention may be hydrates, alkaline salts or acidic salts of 4-quinolone derivatives.

EXAMPLES

The present invention will now be explained more specifically by referring to the following examples.

Example 1

Process for Producing 6,7-Dimethoxy-4-Quinolone

Method 1

Dimethoxyethane (250 ml) was added to 2-amino-4,5-dimethoxy-acetophenone (10.0 g, 51 mol) to form a solution. To this solution was added sodium methoxide (8.3 g, 154 mmol), and the mixture was stirred at room temperature for 70 minutes. Ethyl formate (21 ml, 261 mmol) was then added, and the mixture was stirred at room temperature for an additional 2 hours. After adding water (10 ml) to the reaction solution, and stirring for 25 minutes, 10% hydrochloric acid was added to the mixture for neutralization, thereby causing precipitation. The precipitate was collected by filtration, and washed with water (50 ml×2). The product obtained was dried overnight at 40° C. under reduced pressure to give 10.0 g of the desired product (yield 95%).

Method 2

1,4-Dioxane (100 ml) was added to 2-amino-4,5-dimethoxy-acetophenone (5.0 g, 26 mol) to form a solution. To this solution was added sodium methoxide (4.2 g, 77 mmol), and the mixture was stirred at room temperature for 30 minutes. Ethyl formate (11 ml, 131 mmol) was then added, and the mixture was stirred at room temperature for an additional 55 minutes. After adding water (10 ml) to the reaction solution, and stirring for 10 minutes, 10% hydrochloric acid was added to the mixture for neutralization, thereby causing precipitation. The precipitate was collected by filtration, and washed with water (25 ml×2). The product obtained was dried at 40° C. under reduced pressure to give 5.2 g of the desired product (yield 98%).

Method 3

Toluene (1.2 l) was added to 2-amino-4,5-dimethoxyacetophenone (20.0 g, 103 mmol) to form a solution. To this solution was added sodium hydride (60% in oil; 3.1 g, 76 mmol), and the mixture was stirred at room temperature for 80 minutes. Ethyl formate (42 ml, 520 mmol) was then added, and the mixture was stirred at room temperature for an additional 19 hours. After adding water (400 ml) to the reaction solution, and stirring for 15 minutes, the mixture was separated into a toluene layer and an aqueous layer by fractionation. Water (100 ml) was further added to the toluene layer, and the mixture was fractionated. To the aqueous layers combined was added 10% hydrochloric acid for neutralization, thereby causing precipitation. The precipitate was collected by filtration, and washed with 1,4-dioxane (100 ml) and then with diethyl ether (100 ml). The product obtained was dried under reduced pressure to give 18.4 g of the desired product (yield 87%).

Method 4

Tetrahydrofuran (6 ml) was added to 2-amino-4,5-dimethoxy-acetophenone (300 mg, 1.5 mmol) to form a solution. To this solution was added sodium methoxide (250 mg, 4.6 mmol), and the mixture was stirred at room temperature for 60 minutes. Ethyl formate (0.5 ml, 7.7 mmol) was then added, and the mixture was stirred at room temperature for an additional 150 minutes. After adding water (3 ml) to the reaction solution, and stirring for 30 minutes, 10% hydrochloric acid was added to the mixture for neutralization, thereby causing precipitation. The precipitate was collected by filtration, washed with water (3 ml×2), and then purified by silica gel column chromatography to give 310 mg of the desired product (yield 98%).

$^1$H-NMR (DMSO-$d_6$, 500 MHz): δ 3.82 (s, 3H), 3.86 (s, 3H), 5.94 (d, J=7.3 Hz, 1H), 6.96 (s, 1H), 7.44 (s, 1H), 7.76 (d, J=7.3 Hz, 1H), 11.52 (s, 1H). Mass Spectrometry (FD-MS, m/z): 205 (M$^+$).

Example 2

Process for Producing 4-Quinolone

2-Aminoacetophenone (7.0 g, 52 mmol) was added to and dissolved in 1,4-dioxane (100 ml). To the solution obtained was added sodium methoxide (8.4 g, 156 mmol), and the mixture was stirred at room temperature for 30 minutes. Ethyl formate (21 ml, 261 mmol) was then added, and the mixture was stirred at room temperature for an additional 125 minutes. After adding water (5 ml) to the reaction solution, and stirring for 10 minutes, 10% hydrochloric acid was added to the mixture for neutralization. The reaction solution was then concentrated under reduced pressure. The residue was suspended in chloroform (100 ml), collected by filtration, washed with chloroform (100 ml), and then purified by silica gel column chromatography to give 4.5 g of the desired compound (yield 60%).

$^1$H-NMR (DMSO-$d_6$, 400 MHz): δ 6.02 (d, J=7.6 Hz, 1H), 7.30 (m, 1H), 7.53 (d, J=8.1 Hz, 1H), 7.63 (m, 1H), 7.89 (dd, J=6.1 Hz, 7.3 Hz, 1H), 8.08 (dd, J=1.5 Hz, 8.1 Hz, 1H), 11.74 (brs, 1H). Mass Spectrometry (FD-MS, m/z): 145 (M$^{30}$).

Example 3

Process for Producing 6,7-Methylenedioxy-4-Quinolone

6-Amino-3,4-(methylenedioxy)-acetophenone (5.0 g, 28 mmol) was added to and dissolved in dimethoxyethane (150 ml). To the solution obtained was added sodium methoxide (4.5 g, 84 mmol), and the mixture was stirred at room temperature for 30 minutes. Ethyl formate (12 ml, 143 mmol) was then added, and the mixture was stirred at room temperature for an additional 160 minutes. After adding water (5 ml) to the reaction solution, and stirring for 10 minutes, 10% hydrochloric acid was added to the mixture for neutralization, thereby causing precipitation. The precipitate was collected by filtration, and washed with water (25 ml×2). The product obtained was dried at 40° C. under reduced pressure to give 4.9 g of the desired product (yield 94%).

$^1$H-NMR (DMSO-$d_6$, 500 MHz): δ 5.93 (d, J=7.3 Hz, 1H), 6.12 (s, 2H), 6.97 (s, 1H), 7.38 (s, 1H), 7.75 (d, J=7.3 Hz, 1H), 11.59 (s, 1H). Mass Spectrometry (FD-MS, m/z): 189 (M$^+$).

Example 4

Process for Producing 6-Methyl-4-Quinolone

Toluene (8 mol) was added to 2-amino-5-methylacetophenone (99 mg, 0.67 mmol) to form a solution. To this solution was added sodium hydride (60% in oil; 80 mg, 2 mmol), and the mixture was stirred at room temperature for 30 minutes. Ethyl formate (0.27 ml, 3.3 mmol) was then added, and the mixture was further stirred overnight at room temperature. After adding water (3 ml) to the reaction solution, and stirring for 5 minutes, 10% hydrochloric acid was added to the mixture for neutralization, thereby causing precipitation of crystals. The crystals were collected by filtration, washed with water (3 ml×2), and dried to give 56 mg of the desired product (yield 53%).

$^1$H-NMR (DMSO-$d_6$, 400 MHz): δ 2.40 (s, 3H), 5.99 (dd, J=1.2, J=7.3 Hz, 1H), 7.41–7.49 (m, 2H), 7.84 (dd, J=5.9, 7.3 Hz, 1H), 7.87 (s, 1H), 11.7 (brs, 1H). Mass Spectrometry (FD-MS, m/z): 159 (M$^+$).

Example 5

Process for Producing 7-Fluoro-4-Quinolone

Tetrahydrofuran (4 ml) was added to 2-amino-4-fluoroacetophenone (100 mg, 0.65 mmol) to form a solution. To this solution was added sodium methoxide (106 mg, 1.96 mmol), and the mixture was stirred at room temperature for 60 minutes. Ethyl formate (0.26 ml, 3.27 mmol) was then added, and the mixture was stirred at room temperature for an additional 150 minutes. After adding water (1 ml) to the reaction solution, and stirring for 30 minutes, 10% hydrochloric acid was added to the mixture for neutralization. The neutralized mixture was subjected to extraction with dichloromethane, and the extract was washed with a saturated saline solution, and dried over sodium sulfate. The solution was filtered, and the solvent was distilled off. The residue was purified by silica gel column chromatography to give 53 mg of the desired product (yield 50%).

$^1$H-NMR (DMSO-$d_6$, 400 MHz):δ 6.04 (d, J=7.3 Hz, 1H), 7.17 (dt, J=2.4, 8.8 Hz, 1H), 7.29 (dd, J=2.4, 10.2 Hz, 1H), 7.91 (d, J=7.6 Hz, 1H), 8.14 (dd, J=6.6, 8.8 Hz, 1H), 11.7 (brs, 1H) Mass Spectrometry (FD-MS, m/z): 163 (M$^+$).

INDUSTRIAL APPLICABILITY

According to the process of the present invention, it becomes possible to produce 2,3-unsubstituted 4-quinolone derivatives more simply than ever before and even under milder conditions. It can therefore be said that the process of the instant invention has both commercial and practical values.

What is claimed is:

1. A process for producing a quinolone derivative represented by the formula (I):

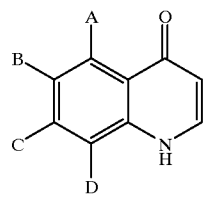

(I)

wherein
A, B, C and D are independently selected from the group consisting of hydrogen, lower alkyl, lower alkoxyl, lower alkylcarbonyl, lower alkoxycarbonyl, lower alkylthio, lower alkylamino, di-lower alkylamino, halogen, trifluoromethyl and nitro, comprising:
reacting a compound represented by the formula (II):

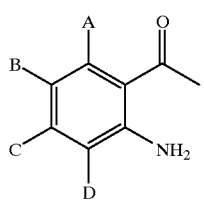

(II)

wherein A, B, C and D are as defined above,
with a formic acid ester in an aprotic solvent selected from the group consisting of aromatic hydrocarbons, ether solvents, acetonitrile and dimethylformamide, in the presence of a base, and
adding a protic solvent to the reaction mixture.

2. The process of claim 1, wherein A, B, C and D are independently hydrogen or a lower alkoxyl.

3. The process of claim 1, wherein the formic acid ester is methyl formate, ethyl formate, propyl formate, isopropyl formate, butyl formate, isobutyl formate, sec-butyl formate, tert-butyl formate or phenyl formate.

4. The process of claim 1, wherein the formic acid ester is methyl formate or ethyl formate.

5. The process of claim 1, wherein the formic acid ester is used in an amount of 3 to 100 equivalents, relative to the compound represented by formula (II).

6. The process of claim 1, wherein the formic acid ester is used in an amount of 5 to 10 equivalents, relative to the compound represented by formula (II).

7. The process of claim 1, wherein the base is a carbonate, a metallic hydride or a metallic alkoxide.

8. The process of claim 1, wherein the base is potassium carbonate, sodium carbonate, cesium carbonate, lithium hydride, sodium hydride, potassium hydride, lithium methoxide, lithium ethoxide, lithium isopropoxide, sodium methoxide, sodium ethoxie, sodium propoxide, sodium isopropoxide, sodium butoxide, sodium isobutoxide, sodium sec-butoxide, sodium tert-butoxide, potassium methoxide, potassium ethoxide, potassium propoxide, potassium isopropoxide, potassium butoxide, potassium isobutoxide, potassium sec-butoxide or potassium tert-butoxide.

9. The process of claim 1, wherein the base is used in an amount of 1 to 20 equivalents, relative to the compound represented by formula (II).

10. The process of claim 1, wherein the base is used in an amount of 2 to 6 equivalents, relative to the compound represented by formula (II).

11. The process of claim 1, wherein the aprotic solvent is benzene, toluene, chlorobenzene, dimethoxyethane, tetrahydrofuran, dioxane, acetonitrile, or dimethylformamide.

12. The process of claim 1, wherein the reaction temperature is in the range of −70 to 150° C., and the reaction time is from 10 minutes to 20 hours.

13. The process of claim 1, wherein the reaction temperature is in the range of 0 to 100° C., and the reaction time is from 10 minutes to 20 hours.

14. The process of claim 1, wherein the protic solvent is used in an amount of 0.01 to 2 times the volume of the aprotic solvent.

15. The process of claim 1, wherein the protic solvent is used in an amount of 0.02 to 1 time the volume of the aprotic solvent.

16. The process of claim 1, wherein the protic solvent is water, methanol, ethanol, propanol, 2-propanol or acetic acid.

17. The process of claim 1, wherein the protic solvent is water.

18. The process of claim 1, wherein, after the addition of the protic solvent, the reaction product is crystallized by further adding to the mixture an aqueous acidic solution.

19. The process of claim 1, wherein, after the addition of the protic solvent, the reaction product is extracted from the mixture with an organic solvent.

20. The process of claim 18, wherein the reaction product obtained is purified by column chromatography, distillation or recrystallization.

21. The process of claim 1, wherein the reaction product obtained is a hydrate, alkaline salt or acidic salt of a 4-quinolone derivative.

* * * * *